United States Patent [19]
Olson et al.

[11] Patent Number: 4,717,780
[45] Date of Patent: Jan. 5, 1988

[54] CATALYTIC AROMATICS CONVERSION

[75] Inventors: David H. Olson, Pennington; Paul G. Rodewald, Rocky Hill, both of N.J.; Ernest W. Valyocsik, Yardley, Pa.

[73] Assignee: Mobil Oil Corp., New York, N.Y.

[21] Appl. No.: 900,047

[22] Filed: Aug. 25, 1986

Related U.S. Application Data

[63] Continuation-in-part of Ser. No. 749,240, Jun. 27, 1985, abandoned, which is a continuation-in-part of Ser. No. 705,821, Feb. 26, 1985, abandoned.

[51] Int. Cl.$^4$ ............................ C07C 2/68; C07C 5/22
[52] U.S. Cl. ..................................... 585/467; 585/475; 585/481
[58] Field of Search ........................ 585/467, 481, 475

[56] References Cited

U.S. PATENT DOCUMENTS

| | | | |
|---|---|---|---|
| 3,702,886 | 11/1972 | Argauer et al. | 423/328 |
| 4,287,166 | 9/1981 | Dwyer et al. | 423/326 |
| 4,427,787 | 1/1984 | Miale et al. | 502/71 |
| 4,483,835 | 11/1984 | Zones | 423/326 |

*Primary Examiner*—Curtis R. Davis
*Attorney, Agent, or Firm*—Alexander J. McKillop; Michael G. Gilman; Dennis P. Santini

[57] ABSTRACT

A process is provided for converting feedstock aromatic compounds by alkylation, transalkylation, disproportionation and/or isomerization over a catalyst comprising zeolite ZSM-58.

32 Claims, No Drawings

CATALYTIC AROMATICS CONVERSION

CROSS-REFERENCE TO RELATED APPLICATION

This application is a continuation-in-part of application Ser. No. 749,240, filed June 27, 1985, and now abandoned, which is a continuation-in-part of application Ser. No. 705,821, filed Feb. 26, 1985, and now abandoned.

BACKGROUND OF THE INVENTION

1 Field of the Invention

This invention relates to a process for converting feedstock comprising aromatic compounds, e.g. benzene and monocyclic alkyl-substituted benzene of from 7 to 12 carbon atoms and mixtures thereof, to product comprising aromatic compounds which differs from said feedstock. The process comprises contacting, under conversion conditions, said feedstock with a catalyst comprising a synthetic, thermally stable, molecular shape selective, active form of crystalline material designated ZSM-58.

2 Description of Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of smaller cavities which may be interconnected by a number of still smaller channels. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as Ca/2, Sr/2, Na, K or Li is equal to unity. One type of cation may be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. These aluminosilicates have come to be designated by convenient symbols, as illustrated by zeolite ZSM-5 (U.S. Pat. No. 3,702,886).

The use of certain zeolites as catalyst components is taught in U.S. Pat. No. 4,305,808, for example.

The silica-to-alumina ratio of a given zeolite is often variable; for example, zeolite X (U.S. Pat. No. 2,882,244) can be synthesized with a silica-to-alumina ratio of from 2 to 3; zeolite Y (U.S. Pat. No. 3,130,007) from 3 to about 6. In some zeolites, the upper limit of silica-to-alumina ratio is virtually unbounded. Zeolite ZSM-5 is one such material wherein the silica-to-alumina ratio is at least 5. U.S. Pat. No. 3,941,871 discloses a crystalline metal organo silicate essentially free of aluminum and exhibiting an x-ray diffraction pattern characteristic of ZSM-5 type aluminosilicate. U.S. Pat. Nos. 4,061,724; 4,073,865 and 4,104,294 describe microporous crystalline silicas or organo silicates wherein the aluminum content present is at impurity levels.

U.S. Pat. No. 4,380,685 teaches para-selective alkylation, transalkylation or disproportionation of a substituted aromatic compound to form a dialkylbenzene compound mixture over catalyst comprising zeolite characterized by a constraint index of 1 to 12 and a silica:alumina mole ratio of at least 12:1, the catalyst having thereon incorporated various metals and phosphorus. Other patents covering alkylation and transalkylation include U.S. Pat. Nos. 4,127,616, 4,361,713, 4,365,104, 4,367,359, 4,370,508 and 4,384,155. Toluene is converted to para-xylene in U.S. Pat. Nos. 3,965,207, 3,965,208, 3,965,209, 4,001,346, 4,002,698, 4,067,920, 4,100,215 and 4,152,364, to name a few. Alkylation with olefins is taught, for example, in U.S. Pat. Nos. 3,962,364 and 4,016,218 and toluene is disproportionated in, for example, U.S. Pat. Nos. 4,052,476, 4,007,231, 4,011,276, 4,016,219 and 4,029,716. Isomerization of xylenes is taught in, for example, U.S. Pat. Nos. 4,100,214, 4,101,595, 4,158,676, 4,159,282, 4,351,979, 4,101,597, 4,159,283, 4,152,363, 4,163,028, 4,188,282 and 4,224,141.

SUMMARY OF THE INVENTION

The present invention relates to a novel process for converting feedstock comprising aromatic compounds selected from the group consisting of benzene, monocyclic alkyl-substituted benzene of from 7 to 12 carbon atoms and mixtures thereof to product comprising aromatic compounds which differs from said feedstock over a catalyst comprising zeolite ZSM-58.

DESCRIPTION OF SPECIFIC EMBODIMENTS

The entire contents of application Ser. No. 705,821, filed Feb. 26, 1985, and application Ser. No. 749,240, filed June 27, 1985, are incorporated herein by reference.

Feedstock aromatic compounds converted hereby include individually and in mixture benzene and monocyclic alkyl-substituted benzene of from 7 to 12 carbon atoms having the structure

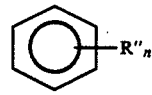

wherein R" is methyl, ethyl or a combination thereof, and n is an integer of from 1 to 4. In other words, the feedstock aromatic compounds may be benzene, benzene containing from 1 to 4 methyl and/or ethyl group substituents, and mixtures thereof. Non-limiting examples of such feedstock compounds include benzene, toluene, xylene, ethylbenzene, mesitylene (1,3,5-trimethylbenzene), durene (1,2,4,5-tetramethylbenzene), pseudocumene (1,2,4-trimethylbenzene) and mixtures thereof.

Other reactant species may be present, such as for alkylation. Alkylating agent species include olefins such as ethylene, propylene, dodecylene, as well as formaldehyde, alkyl halides, alcohols and ethers; the alkyl portion thereof having from 1 to 24 carbon atoms. Numerous other acyclic compounds having at least one reactive alkyl radical may be utilized as alkylating agents.

Products of the present conversion process include alkyl-substituted benzene compounds which differ from feedstock compounds depending upon the conversion desired. The following listing presents non-limiting examples:

| Feedstock Aromatic Compounds Include | Other Reactants Include | Product Aromatic Compounds Include |
|---|---|---|
| Benzene | Ethylene | Ethylbenzene |
| Toluene | Methanol | Xylene isomers |
| Xylene isomers, e.g., 9:73:18 wt. ratio of para:meta:ortho | — | Different combination of xylene isomers, e.g. 23:57:20 wt. ratio of para:meta:ortho |
| Toluene | — | Benzene and xylenes |
| Benzene | Propylene | Cumene and diisopropylbenzene |
| Toluene | Propylene | Cymene isomers |

Mechanisms of the present process may be isomerization, alkylation, transalkylation and disproportionation. Disproportionation is a special case of transalkylation in which the alkylatable aromatic compound and the transalkylating agent is the same compound, for example, when toluene serves as the donor and acceptor of a transferred methyl group to produce benzene and xylene. Use of the term transalkylation includes the special case of disproportionation.

In general, the present process is conducted at conversion conditions sufficient to convert the above feedstock to the indicated product including a temperature of from about 150° C. to about 760° C., a pressure of from about 0 psig to about 2950 psig, a weight hourly space velocity of from about 0.1 hr$^{-1}$ to about 2000 hr$^{-1}$ and a hydrogen/feedstock hydrocarbon compound mole ratio of from 0 (no added hydrogen) to about 100.

Such conversion process includes, as non-limiting examples, isomerizing xylene feedstock components to product enriched in p-xylene with reaction conditions including a temperature from about 150° C. to about 600° C., a pressure of from about 0 psig to about 1000 psig, a weight hourly space velocity of from about 0.1 hr$^{-1}$ to about 200 hr$^{-1}$ and a hydrogen/hydrocarbon mole ratio of from about 0 to about 100; disproportionating toluene to product comprising benzene and xylenes with reaction conditions including a temperature of from about 200° C. to about 760° C., a pressure of from about 14 psig to about 900 psig and a weight hourly space velocity of from about 0.1 hr$^{-1}$ to about 20 hr$^{-1}$; alkylating aromatic hydrocarbons, e.g. benzene and alkylbenzenes, in the presence of an alkylating agent, e.g. olefins, formaldehyde, alkyl halides and alcohols, with reaction conditions including a temperature of from about 150° C. to about 650° C., a pressure of from about 14 psig to about 2950 psig, a weight hourly space velocity of from about 2 hr$^{-1}$ to about 2000 hr$^{-1}$ and a feedstock aromatic hydrocarbon/alkylating agent mole ratio of from about 1/1 to about 20/1; and transalkylating aromatic hydrocarbons in the presence of polyalkylaromatic hydrocarbons with reaction conditions including a temperature of from about 200° C. to about 760° C., a pressure of from about 14 psig to about 2950 psig, a weight hourly space velocity of from about 10 hr$^{-1}$ to about 1000 hr$^{-1}$ and a feedstock aromatic hydrocarbon/polyalkylaromatic hydrocarbon mole ratio of from about 1/1 to about 16/1.

The present process requires a catalyst comprising the synthetic, thermally stable, molecular shape selective crystalline ZSM-58.

The structure of ZSM-58 is distinguished from other crystalline silicates by a unique X-ray diffraction pattern. Characteristic X-ray diffraction pattern intensities of ZSM-58 are substantially shown in Table 1, hereinafter.

The crystalline silicate ZSM-58 has a composition involving silica and alumina in the relationship $$(0.1-2)Al_2O_3:(100)SiO_2.$$

In the as-synthesized form, ZSM-58 has a formula, on an anhydrous basis and in terms of moles of oxides per 100 moles of silica, as follows:

$$(0.1-2.0)R_2O:(0.02-1.0)M_{2/n}O:(0.1-2)Al_2O_3:(100)SiO_2$$

wherein M is an alkali or alkaline earth metal cation, n is the valence of M, and R is an organic cation.

TABLE 1

| Interplanar d-Spacing (A) | Relative Intensity, I/Io |
|---|---|
| 13.70 ± 0.20 | W |
| 11.53 ± 0.20 | W-VS |
| 10.38 ± 0.20 | W |
| 7.82 ± 0.14 | W-VS |
| 6.93-6.79 ± 0.14 | W-VS |
| 6.19 ± 0.14 | W-VS |
| 5.94 ± 0.12 | W-M |
| 5.77 ± 0.12 | VS |
| 5.22 ± 0.12 | W |
| 5.18 ± 0.10 | VS |
| 4.86 ± 0.09 | M-S |
| 4.72 ± 0.08 | S |
| 4.57 ± 0.08 | W |
| 4.51 ± 0.08 | S |
| 4.43 ± 0.08 | W |
| 4.19 ± 0.08 | W |
| 4.15 ± 0.08 | M |
| 4.00 ± 0.07 | W |
| 3.97 ± 0.07 | W |
| 3.89 ± 0.07 | W |
| 3.84 ± 0.07 | M |
| 3.81 ± 0.07 | W-M |
| 3.59 ± 0.06 | W |
| 3.46 ± 0.06 | W-M |
| 3.41 ± 0.06 | S-VS |
| 3.36 ± 0.06 | S-VS |
| 3.32 ± 0.06 | M-S |
| 3.29 ± 0.05 | W |
| 3.17 ± 0.05 | W-M |
| 3.07 ± 0.05 | W-M |
| 3.05 ± 0.05 | W-M |
| 3.01 ± 0.05 | W-M |
| 2.88 ± 0.05 | W |
| 2.85 ± 0.05 | W |
| 2.75 ± 0.05 | W |
| 2.67 ± 0.04 | W |
| 2.60 ± 0.04 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Table 1, the relative intensities are given in terms of the symbols W=weak, M=medium, S=strong and VS=very strong. In terms of intensities, these may be generally designated as follows:

W=0–20

M=20–40

S=40–60

VS=60–100

It should be understood that this X-ray diffraction pattern is characteristic of all the species of ZSM-58 compositions. The sodium form as well as other cationic forms reveal substantially the same pattern with some minor shifts in interplanar spacing and variation in relative intensity. Other minor variations can occur, depending on the silicon to aluminum ratio of the particular sample, as well as its degree of thermal treatment. Multiplets may be observed in the typical X-ray pattern for ZSM-58 at d-spacing values of 6.93–6.79±0.14, 4.86±0.09, 3.41±0.06, 3.07±0.05 and 3.01±0.05 Angstroms.

The original alkali or alkaline earth metal cations of the as-synthesized ZSM-58 can be replaced in accordance with techniques well known in the art, at least in part, by ion exchange with other cations. Preferred replacing cations include metal ions, hydrogen ions, hydrogen precursor, e.g. ammonium, ions and mixtures thereof. Particularly preferred cations are those which render the ZSM-58 more catalytically active for the present reaction. These include hydrogen, rare earth metals and metals of Groups IIA, IIIA, IVA, IB, IIB, IIIB, IVB, VIB and VIII of the Periodic Table of the Elements.

Typical ion exchange technique would be to contact the synthetic ZSM-58 with a salt of the desired replacing cation or cations. Examples of such salts include the halides, e.g. chlorides, nitrates and sulfates.

The crystalline silicate ZSM-58 can also be used in the present process in intimate combination with a hydrogenating component such as tungsten, vanadium, molybdenum, rhenium, nickel, cobalt, chromium, manganese, or a noble metal such as platinum. Such component can be exchanged into the composition to the extent aluminum is in the structure, impregnated therein or intimately physically admixed therewith. Such component can be impregnated in or on to it such as for example, by, in the case of platinum, treating the ZSM-58 with a solution containing a platinum metal-containing ion. Thus, suitable platinum compounds include chloroplatinic acid, platinous chloride and various compounds containing the platinum amine complex.

The crystalline silicate ZSM-58, especially in its metal, hydrogen and ammonium forms can be beneficially converted to another form by thermal treatment. This thermal treatment is generally performed by heating one of these forms at a temperature of at least 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product is particularly useful in the present process.

The ZSM-58 should be dehydrated, at least partially. This can be done by heating to a temperature in the range of 200° C. to 595° C. in an inert atmosphere, such as air, nitrogen, etc. and at atmospheric, subatmospheric or superatmospheric pressures for between 30 minutes and 48 hours. Dehydration can also be performed at room temperature merely by placing ZSM-58 in a vacuum, but a longer time is required to obtain a sufficient amount of dehydration.

The ZSM-58 can be prepared from a reaction mixture containing sources of an alkali or alkaline earth metal (M) cation, an oxide of aluminum, an oxide of silicon, an organic cation (R) of a methyltropinium salt, e.g. halide, hydroxide, sulfate, etc., and water, said reaction mixture having a composition, in terms of mole ratios of oxides, within the following ranges:

| Reactants | Useful | Preferred |
| --- | --- | --- |
| $SiO_2/Al_2O_3$ | 50–1000 | 70–500 |
| $H_2O/SiO_2$ | 5–200 | 10–100 |
| $OH^-/SiO_2$ | 0–2.0 | 0.10–1.0 |
| $M/SiO_2$ | 0.01–3.0 | 0.10–1.0 |
| $R/SiO_2$ | 0.01–2.0 | 0.10–0.50 | wherein R and M are as above defined.

Crystallization of the ZSM-58 can be carried out at either static or stirred condition in a suitable reactor vessel, such as for example, polypropylene jars or teflon lined or stainless steel autoclaves. The total useful range of temperatures for crystallization is from about 80° C. to about 25° C. for a time sufficient for crystallization to occur at the temperature used, e.g. from about 24 hours to about 60 days. Thereafter, the crystals are separated from the liquid and recovered. The reaction mixture can be prepared utilizing materials which supply the appropriate oxides. Such materials may include sodium silicate, silica hydrosol, silica gel, silicic acid, sodium hydroxide, a source of aluminum, and the methyltropinium salt directing agent. The methyltropinium salt may be synthesized by selective methylation of 3-tropanol at the bridgehead nitrogen. This salt has the following formula:

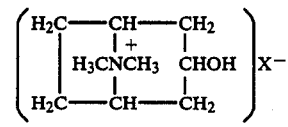

wherein X is an anion, such as, for example, a halide (e.g. iodide, chloride or bromide), nitrate, hydroxide, sulfate, bisulfate, perchlorate, etc. U.S. application Ser. No. 705,820, filed Feb. 26, 1985 teaches these salts and their synthesis and is incorporated herein by reference.

It should be realized that the reaction mixture oxides can be supplied by more than one source. The reaction mixture can be prepared either batchwise or continuously. Crystal size and crystallization time of the new crystalline material will vary with the nature of the reaction mixture employed and the crystallization conditions.

In all cases, synthesis of the ZSM-58 crystals is facilitated by the presence of at least 0.01 percent, preferably 0.10 percent and still more preferably 1 percent, seed crystals (based on total weight) of crystalline product.

The crystals prepared as above can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

In practicing the desired chemical conversion process, it may be useful to composite the crystalline zeolite ZSM-58 with matrix-comprising material resistant to the temperature and other conditions employed in the process. Such matrix material is useful as a binder and imparts additional resistance to the catalyst for the temperature, pressure and reactant feed stream velocity conditions allowed in the present process. The composite may be in the form of an extrudate.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families which include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing matrix materials, the catalyst employed herein may be composited with a porous matrix material such as alumina, silica, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of activity enhanced zeolite component and matrix, on an anhydrous basis, may vary widely with the zeolite content of the dry composite ranging from about 1 to about 99 percent by weight and more usually in the range of about 5 to about 80 percent by weight.

In order to more fully illustrate the nature of the invention and the manner of practicing same, the following examples are presented. In the examples, whenever sorption data are set forth for comparison of sorptive capacities for cyclohexane and/or n-hexane, they were measured on an electrobalance as follows:

The adsorbate was activated at 500° C. in flowing helium until at constant weight. Adsorptions were conducted at 90° C., with the hydrocarbon containing helium gas stream flowing around the sample. Partial pressures of hexane and cyclohexane were 28 and 35 torr, respectively. The measurements were continued until the sample reached constant weight. The increase in weight was converted to adsorption capacity of the sample in g/100 g of activated zeolite.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078 and in *The Journal of Catalysis*, Vol. IV, pp. 527-529 (August 1965), each incorporated herein as to that description. The relationship of Alpha Value to the intrinsic rate constants for many acid-catalyzed reactions, such as that of the present invention, is detailed in "The Active Site of Acidic Aluminosilicate Catalysts," Nature, Vol. 309, No. 5969, pp. 589-591, 14 June 1984, incorporated herein by reference as to that detail.

EXAMPLES 1-6

Six separate synthesis reaction mixtures were prepared with compositions indicated in Table 2. The mixtures were prepared with silica sol (30 percent $SiO_2$), $NaAlO_2$, NaOH, a methyltropinium salt, i.e. iodide, and water. The mixtures were maintained at 160° C. for 4 days in a stainless steel, stirred (400 rpm) autoclave at autogenous pressure. Solids were separated from any unreacted components by filtration and then water washed, followed by drying at 110° C. The product crystals were analyzed by X-ray diffraction and chemical analysis. The product of Example 1 was found to be crystalline ZSM-58 with a trace of unidentified second component impurity. The products from Examples 2-6 proved to be 100 percent crystalline ZSM-58.

The X-ray diffraction pattern of the Example 4 crystals, after calcination at 538° C. for 17 hours in air, is set forth as illustration in Table 3. Other properties of each crystalline product are presented in Table 4. In the latter table, compositions are calculated on the basis of 100 ($SiO_2$ +$AlO_2^-$) tetrahedra. The as-synthesized ZSM-58 from these examples contains from 3.8 to 5.0 methyltrophinium cations per 100 tertrahedra.

TABLE 2

| | Mixture Composition (mole ratios) | | | | |
|---|---|---|---|---|---|
| Example | $\dfrac{SiO_2}{Al_2O_3}$ | $\dfrac{H_2O}{SiO_2}$ | $\dfrac{OH^-}{SiO_2}$ | $\dfrac{Na^+}{SiO_2}$ | $\dfrac{R^*}{SiO_2}$ |
| 1 | 300 | 40 | 0.30 | 0.31 | 0.25 |
| 2 | 200 | 40 | 0.30 | 0.31 | 0.25 |
| 3 | 90 | 40 | 0.40 | 0.42 | 0.25 |
| 4 | 90 | 40 | 0.30 | 0.32 | 0.25 |
| 5 | 90 | 40 | 0.30 | 0.32 | 0.25 |
| 6 | 70 | 40 | 0.30 | 0.33 | 0.25 |

*R = methyltropinium cation.

TABLE 3

| d(A) | Observed 2 Theta | Relative Intensity |
|---|---|---|
| 13.57 | 6.511 | 7.4 |
| 11.44 | 7.721 | 51.2 |
| 10.29 | 8.588 | 4.1 |
| 7.76 | 11.389 | 53.6 |
| 6.89 | 12.834 | 60.1 |
| 6.84 | 12.932 | 33.0 |
| 6.15 | 14.378 | 57.8 |
| 5.91 | 14.987 | 19.5 |
| 5.74 | 15.435 | 85.8 |
| 5.16 | 17.173 | 100.0 |
| 4.84 | 18.317 | 51.9 |
| 4.70 | 18.865 | 56.0 |
| 4.52 | 19.612 | 20.3 |
| 4.49 | 19.755 | 51.7 |
| 4.41 | 20.093 | 4.7 |
| 4.13 | 21.486 | 26.0 |

TABLE 3-continued

| d(A) | Observed 2 Theta | Relative Intensity |
|---|---|---|
| 3.98 | 22.307 | 11.8 |
| 3.96 | 22.404 | 8.9 |
| 3.87 | 22.969 | 17.1 |
| 3.82 | 23.268 | 30.6 |
| 3.80 | 23.365 | 25.6 |
| 3.57 | 24.882 | 16.2 |
| 3.44 | 25.849 | 35.2 |
| 3.38 | 26.303 | 96.5 |
| 3.35 | 26.546 | 86.7 |
| 3.34 | 26.619 | 80.8 |
| 3.30 | 26.947 | 66.2 |
| 3.28 | 27.158 | 9.1 |
| 3.16 | 28.237 | 23.3 |
| 3.06 | 29.159 | 26.8 |
| 3.06 | 29.176 | 31.2 |
| 3.03 | 29.406 | 22.7 |
| 2.996 | 29.816 | 25.2 |
| 2.988 | 29.901 | 21.2 |
| 2.870 | 31.158 | 4.1 |
| 2.842 | 31.473 | 5.1 |
| 2.664 | 33.638 | 5.5 |
| 2.589 | 34.643 | 4.8 |
| 2.503 | 35.869 | 4.3 |
| 2.488 | 36.099 | 6.3 |
| 2.438 | 36.863 | 9.0 |
| 2.421 | 37.134 | 14.9 |
| 2.390 | 37.626 | 5.8 |
| 2.354 | 38.230 | 2.8 |
| 2.332 | 38.591 | 4.3 |
| 2.300 | 39.161 | 16.7 |
| 2.236 | 40.319 | 2.4 |
| 2.231 | 40.413 | 1.9 |
| 2.211 | 40.807 | 3.2 |
| 2.164 | 41.739 | 1.7 |
| 2.111 | 42.836 | 1.4 |
| 2.073 | 43.660 | 3.0 |
| 2.039 | 44.427 | 0.3 |
| 1.977 | 45.880 | 11.4 |
| 1.950 | 46.568 | 4.4 |
| 1.932 | 47.030 | 3.9 |
| 1.915 | 47.476 | 3.7 |
| 1.838 | 49.594 | 6.4 |
| 1.835 | 49.667 | 5.5 |

TABLE 4

| Example | Moles C Mole N | Moles per Mole $Al_2O_3$ | | | COMPOSITION | | | |
|---|---|---|---|---|---|---|---|---|
| | | $N_2O$ | $Na_2O$ | $SiO_2$ | Al 100 $T_d$ | $Na^+$ 100 $T_d$ | $N^+$ 100 $T_d$ | R 100 $T_d$ |
| 1 | 9.5 | 4.09 | 0.85 | 223 | 0.89 | 0.76 | 3.6 | 3.8 |
| 2 | 11.2 | 2.43 | 0.74 | 140 | 1.4 | 1.0 | 3.4 | 4.2 |
| 3 | 9.6 | 1.85 | 0.13 | 83 | 2.4 | 0.30 | 4.4 | 4.7 |
| 4 | 10.2 | 1.69 | 0.12 | 78 | 2.5 | 0.30 | 4.2 | 4.8 |
| 5 | 10.8 | 1.77 | 0.25 | 85 | 2.3 | 0.58 | 4.1 | 4.9 |
| 6 | 9.6 | 1.50 | 0.10 | 62 | 3.1 | 0.30 | 4.7 | 5.0 |

EXAMPLE 7

A sample of the Example 4 product crystals, having been calcined in nitrogen for 4 hours at 500° C., ammonium exchanged and then converted to the hydrogen form, was subjected to the sorption test. Significant n-hexane, i.e. 8 weight percent at 90° C., was sorbed while only minimal cyclohexane (about 1 weight percent at 90° C.) was sorbed. This indicates molecular shape selectivity for the ZSM-58.

EXAMPLE 8

The sample of Example 4 product used for sorption evaluation was evaluated in the Alpha Test. Its Alpha Value proved to be 13 at 538° C.

EXAMPLES 9-19

A feedstock comprising $C_8$ aromatic compounds, see Table 5, was passed over catalyst comprising the ZSM-58 product crystals from Example 4, calcined and converted to the hydrogen form in Example 7, at 483° C., 400 psig, a hydrogen/hydrocarbon ratio of 4/1 and a weight hourly space velocity varied for Examples 9-19 between 2 and 16. Reaction product compositions are given in Table 5. As can be seen from the data provided in Table 5, at a weight hourly space velocity of 4 hr$^{-1}$, near equilibrium (95%) p-xylene levels were achieved along with about 25% conversion of the ethylbenzene. Xylene loss levels were good, below about 3% at this conversion level.

TABLE 5

| Example | Feed | 9 | 10 | 11 | 12 | 13 | 14 | 15 | 16 | 17 | 18 | 19 |
|---|---|---|---|---|---|---|---|---|---|---|---|---|
| TOS (hr) | | 2.03 | 4.03 | 5.72 | 9.72 | 14.74 | 16.26 | 17.78 | 20.80 | 25.82 | 27.33 | 28.88 |
| Temp. (°C.) | | 483 | 483 | 483 | 483 | 483 | 483 | 483 | 483 | 483 | 483 | 483 |
| Press. (psig) | | 400 | 400 | 400 | 400 | 400 | 400 | 400 | 400 | 400 | 400 | 400 |
| $H_2$/HC (molar) | | 4 | 4 | 4 | 4 | 4 | 4 | 4 | 4 | 4 | 4 | 4 |
| WHSV (hr$^{-1}$) | | 4 | 4 | 8 | 4 | 2 | 8 | 16 | 4 | 2 | 8 | 16 |
| Liquid Product Analysis (wt. %) | | | | | | | | | | | | |
| Light gas | | 0.74 | 0.60 | 0.62 | 1.19 | 3.01 | 0.50 | 0.30 | 0.47 | 1.58 | 0.37 | 0.26 |
| Benzene | 0.4 | 4.43 | 4.05 | 2.88 | 4.88 | 7.56 | 2.30 | 1.27 | 2.69 | 4.68 | 1.79 | 1.02 |
| Toluene | 0.10 | 1.44 | 1.42 | 0.79 | 1.36 | 2.26 | 0.65 | 0.44 | 0.91 | 1.50 | 0.54 | 0.39 |
| EB | 24.74 | 18.94 | 18.57 | 20.64 | 18.19 | 16.66 | 21.36 | 22.77 | 20.20 | 18.31 | 21.86 | 23.04 |
| p-xylene | 0.93 | 16.39 | 16.39 | 15.68 | 16.44 | 15.94 | 14.19 | 10.35 | 14.67 | 15.44 | 12.34 | 8.29 |
| | (1.2) | (22.6) | (22.7) | (21.5) | (22.8) | (23.4) | (19.3) | (14.0) | (20.0) | (21.8) | (16.7) | (11.2) |
| m-xylene | 47.87 | 38.41 | 38.22 | 38.22 | 36.83 | 35.52 | 39.25 | 41.82 | 39.48 | 37.04 | 40.53 | 43.32 |
| | (63.7) | (53.0) | (53.0) | (52.4) | (51.1) | (52.1) | (53.3) | (56.4) | (53.8) | (52.3) | (54.8) | (58.3) |
| o-xylene | 26.32 | 17.63 | 17.54 | 19.04 | 18.86 | 16.75 | 20.14 | 22.04 | 19.30 | 18.34 | 21.14 | 22.74 |
| | (35.0) | (24.3) | (24.3) | (26.1) | (26.2) | (24.6) | (27.4) | (29.7) | (26.3) | (25.9) | (28.6) | (30.6) |
| $C_9$+ (total) | | 1.99 | 3.06 | 2.10 | 2.23 | 2.29 | 1.57 | 0.98 | 2.25 | 2.69 | 1.40 | 0.90 |
| Total xylenes | 75.12 | 72.43 | 72.15 | 72.94 | 72.13 | 68.21 | 73.58 | 74.21 | 73.45 | 70.82 | 74.01 | 74.35 |
| p-xyl (% of Equil.) | 5.2 | 94.3 | 94.6 | 89.6 | 95.0 | 97.37 | 80.4 | 58.1 | 83.2 | 90.8 | 69.5 | 46.5 |

TABLE 5-continued

| Example | Feed | 9 | 10 | 11 | 12 | 13 | 14 | 15 | 16 | 17 | 18 | 19 |
|---|---|---|---|---|---|---|---|---|---|---|---|---|
| EB/EB (%) | | 23.4 | 24.9 | 16.6 | 26.5 | 32.7 | 13.7 | 8.0 | 18.4 | 26.0 | 11.6 | 6.9 |

EXAMPLES 20–21

Toluene was disproportionated over catalyst comprising the hydrogen-form of ZSM-58 prepared in Example 7 at two different weight hourly space velocities of 6 hr$^{-1}$ (Example 20) and 1 hr$^{-1}$ (Example 21). Reaction conditions included a temperature of 550° C. and atmospheric pressure. Results, listed in Table 6, indicate that the ZSM-58 becomes more p-selective at lower toluene conversion.

TABLE 6

| Example | Conversion wt % | Selectivity, Wt. % | | | |
|---|---|---|---|---|---|
| | | Benzene | p-xylene | m-xylene | o-xylene |
| 20 | 1.4 | 45 | 21[a] | 26 | 8 |
| 21 | 7.4 | 44 | 14[b] | 29 | 13 |

[a] p-xylene in xylenes = 38% (Thermodynamic p-xylene in xylenes = 25%)
[b] p-xylene in xylenes = 25%

EXAMPLE 22

Alkylation of toluene with methanol alkylating agent was conducted over catalyst comprising the hydrogen-form of ZSM-58 prepared as in Example 7 at 500° C. and atmospheric pressure. The weight hourly space velocity was maintained at 12 hr$^{-1}$ and the mole ratio of toluene to methanol was 4/1. Toluene conversion was 10 wt. % with significant selectivity to xylenes, especially the para-isomer, indicated. The xylenes product was composed of 58 wt % p-xylene, 25 wt % m-xylene and 17 wt % o-xylene. The 58 wt % para-isomer compares to a thermodynamic equilibrium value of only 25 wt %.

What is claimed is:

1. A process for converting feedstock comprising aromatic compounds selected from the group consisting of benzene, monocyclic alkyl-substituted benzene of from 7 to 12 carbon atoms and mixtures thereof, alkyl being methyl, ethyl or a combination thereof, to alkylation conversion product comprising aromatic compounds which differs from said feedstock, which comprises contacting said feedstock and an alkylating agent at conversion conditions sufficient to convert said feedstock to said product with a catalyst composition comprising zeolite ZSM-58.

2. The process of claim 1 wherein said zeolite has been treated to replace orignal cations, at least in part, with a cation or mixture of cations selected from the group consisting of hydrogen, hydrogen precursors, rare earth metals, and metals of Groups IIA, IIIA, IVA, IB, IIB, IIIB, IBV, VIB and VIII ofthe Periodic Table.

3. The process of claim 2 wherein said replacement cations comprise hydrogen or a hydrogen precursor.

4. The process of claim 1 wherein said catalyst composition comprises said zeolite and a matrix.

5. The process of claim 4 wherein said catalyst composition is in the form of an extrudate.

6. The process of claim 4 wherein said catalyst composition is in the form of beads.

7. The process of claim 4 wherein said matrix is alumina-containing material.

8. The process of claim 1 wherein said conversion conditions include a temperature of from about 150° C. to about 650° C., a pressure of from about 14 psig to about 2950 psig, a weight hourly space velocity of from about 2 hr$^{-1}$ to about 2000 hr$^{-1}$ and a feedstock aromatic compound/alkylating agent mole ratio of from about 1/1 to about 20/1.

9. A process for converting feedstock comprising toluene to disproportionation conversion product which comprises contacting said feedstock at conversion conditions sufficient to convert said feedstock to said product with a catalyst composition comprising zeolite ZSM-58.

10. The process of claim 9 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

11. The process of claim 10 wherein said replacement cations comprise hydrogen or a hydrogen precursor.

12. The process of claim 9 wherein said catalyst composition comprises said zeolite and a matrix.

13. The process of claim 12 wherein said catalyst composition is in the form of an extrudate.

14. The process of claim 12 wherein said catalyst composition is in the form of beads.

15. The process of claim 12 wherein said matrix is alumina-containing material.

16. The process of claim 9 wherein said conversion conditions include a temperature of from about 200° C. to about 760° C., a pressure of from about 14 psig to about 900 psig and a weight hourly space velocity of from about 0.1 hr$^{-1}$ to about 20 hr$^{-1}$.

17. A process for converting feedstock comprising xylene isomers to isomerization conversion product which comprises contacting said feedstock at conversion conditions sufficient to convert said feedstock to said product with a catalyst composition comprising zeolite ZSM-58.

18. The process of claim 17 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

19. The process of claim 18 wherein said replacement cations comprise hydrogen or a hydrogen precursor.

20. The process of claim 17 wherein said catalyst composition comprises said zeolite and a matrix.

21. The process of claim 20 wherein said catalyst composition is in the form of an extrudate.

22. The process of claim 20 wherein said catalyst composition is in the form of beads.

23. The process of claim 20 wherein said matrix is alumina-containing material.

24. The process of claim 17 wherein said conversion conditions include a temperature of from about 150° C. to about 600° C., a pressure of from about 0 psig to about 1000 psig, a weight hourly space velocity of from about 0.1 hr$^{-1}$ to about 200 hr$^{-1}$ and a hydrogen/hydrocarbon mole ratio of from 0 to about 100.

25. A process for converting feedstock comprising an aromatic hydrcarbon compound and a polyalkylaromatic hydrocarbon compound, alkyl being methyl, ethyl or a combination thereof, to transalkylation conversion product which comprises contacting said feedstock at conversion conditions sufficient to convert said feedstock to said product with a catalyst composition comprising zeolite ZSM-58.

26. The process of claim 25 wherein said zeolite has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

27. The process of claim 26 wherein said replacement cations comprise hydrogen or a hydrogen precursor.

28. The process of claim 25 wherein said catalyst composition comprises said zeolite and a matrix.

29. The process of claim 27 wherein said matrix is alumina-containing material.

30. The process of claim 28 wherein said catalyst composition is in the form of an extrudate.

31. The process of claim 28 wherein said catalyst composition is in the form of beads.

32. The process of claim 25 wherein said conversion conditions include a temperature of from about 200° C. to about 760° C., a pressure of from about 14 psig to about 2950 psig, a weight hourly space velocity of from about 10 $hr^{-1}$ to about 1000 $hr^{-1}$ and a feedstock aromatic hydrocarbon/polyalkylaromatic hydrocarbon mole ratio of from about 1/1 to about 16/1.

* * * * *

UNITED STATES PATENT AND TRADEMARK OFFICE
CERTIFICATE OF CORRECTION

PATENT NO. : 4,717,780

DATED : January 5, 1988

INVENTOR(S) : David H. Olson et al

It is certified that error appears in the above-identified patent and that said Letters Patent is hereby corrected as shown below:

Col. 6, line 37, "25°C" should be --225°C--
Col. 11, claim 2, line 55, "IBV" should be --IVB--
Col. 11, claim 2, line 55, "ofthe" should be --of the--

Signed and Sealed this

Sixth Day of September, 1988

Attest:

DONALD J. QUIGG

*Attesting Officer*     *Commissioner of Patents and Trademarks*